United States Patent [19]

Marker et al.

[11] Patent Number: 5,473,105

[45] Date of Patent: Dec. 5, 1995

[54] PROCESS FOR CONCURRENTLY PRODUCING DIISOPROPYL ETHER AND ISOPROYL ETHYL ETHER

[75] Inventors: Terry L. Marker, Warrenville; Robert J. Schmidt, Barrington; Richard E. Marinangeli, Arlington Heights; Allyn T. Gilbert, Mount Prospect, all of Ill.

[73] Assignee: UOP, Des Plaines, Ill.

[21] Appl. No.: 317,448

[22] Filed: Oct. 4, 1994

[51] Int. Cl.$^6$ .................................................. C07G 41/05
[52] U.S. Cl. ........................ 568/697; 568/671; 568/689; 568/694
[58] Field of Search .................................... 568/671, 689, 568/694, 585, 671, 689, 579, 697

[56] References Cited

U.S. PATENT DOCUMENTS

| | | | |
|---|---|---|---|
| 4,256,465 | 3/1981 | Takezone et al. | 568/689 |
| 4,503,263 | 3/1985 | Olah | 568/694 |
| 4,714,787 | 12/1987 | Bell et al. | 568/697 |
| 4,843,180 | 6/1989 | Mullins | 568/689 |
| 4,857,664 | 8/1989 | Huang et al. | 568/695 |
| 4,906,787 | 3/1990 | Huang et al. | 568/697 |
| 4,935,552 | 6/1990 | Child et al. | 568/695 |
| 5,371,301 | 12/1994 | Marker et al. | 568/694 |
| 5,374,301 | 12/1994 | Marker et al. | 568/694 |

*Primary Examiner*—Werren B. Lone
*Attorney, Agent, or Firm*—Thomas K. McBride; Eugene I. Snyder

[57] ABSTRACT

A process for concurrently producing diisopropyl ether and isopropyl ethyl ether from water, ethanol from an independent source, and propylene, has been developed. The product mixture may be used as a high octane number booster due mainly to the presence of the diisopropyl ether and to a lesser extent, the isopropyl ethyl ether. Furthermore, the product mixture, upon blending with gasoline, incorporates a renewable resource into the gasoline since the isopropyl ethyl ether is produced from ethanol. Optionally, the product mixture may be passed through an acid removal zone to remove acid, if present, before being recycled or further processed. A portion of the product mixture is recycled to the reaction zone to increase the conversion of reactants to products.

18 Claims, 1 Drawing Sheet

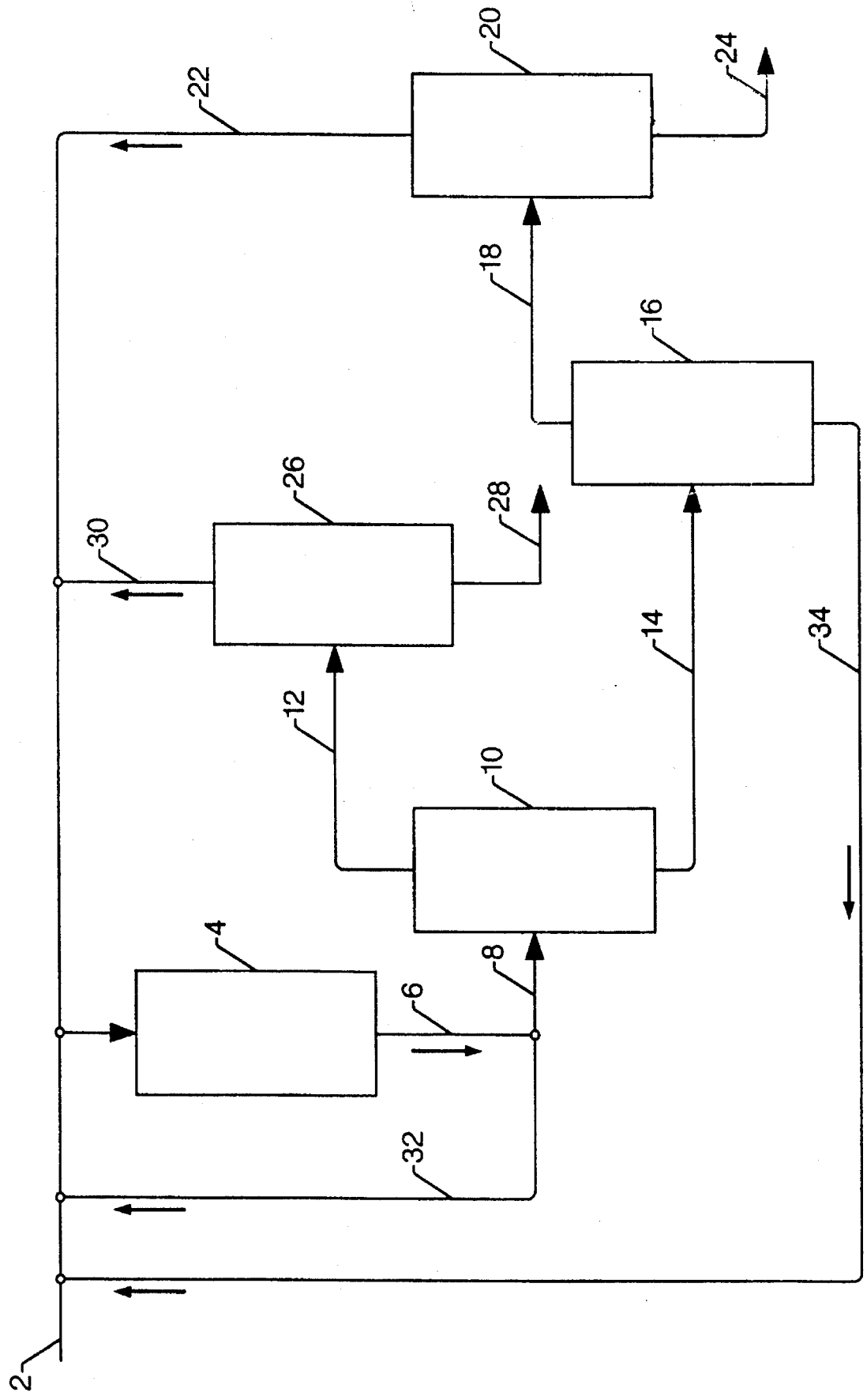

PROCESS FOR CONCURRENTLY PRODUCING DIISOPROPYL ETHER AND ISOPROYL ETHYL ETHER

BACKGROUND OF THE INVENTION

The growing concern for protecting natural resources has prompted various initiatives, one of which is a drive to incorporate renewable resources into gasoline. Adding methanol or ethanol to gasoline to boost the octane number is an example of a response to this need to conserve finite resources. However, a major drawback to this practice is that the alcohol cannot be added prior to the gasoline being transported through a pipeline since the alcohol is water-soluble and will extract out of the gasoline and into any water that might be present in the pipeline system or storage tanks. The present invention provides an alternate method that achieves the conservation goal. Furthermore, the resultant blended gasoline may be transported through a pipeline without the loss of octane number boosters. According to the present invention, ethanol, which is a renewable resource since it may be produced from corn, undergoes etherification with propylene to produce isopropyl ethyl ether (IPEE) which may then be blended into gasoline. An additional benefit of blending ethers into gasoline to boost the octane number is that ethers generally have lower Reid vapor pressures than alcohols, and lowering the Reid vapor pressures of gasoline is another environmentally driven goal.

The octane number of IPEE is less than another commonly used octane number booster, diisopropyl ether (DIPE), which has an octane number of about 105, (R+M)/2. DIPE and IPEE are produced in similar manners, and being able to produce them concurrently satisfies both the desire for high octane number boosters and the need to incorporate a renewable resource into the gasoline. Furthermore, the gasoline after being blended with DIPE and IPEE, may be transported through pipelines since the ethers are not very water soluble.

The art shows various processes for the production of ethers. For example, U.S. Pat. No. 4,906,787 discloses a process where in a reaction zone at least one light olefin is hydrated to form at least one alcohol which then undergoes etherification with the olefin to produce an ether. Unreacted alcohol is recycled to the reaction zone. It is important to note that in this patent all the alcohol that is reacted with the olefin to form ether is produced within the process. No external source of alcohol is used. Similarly, U.S. Pat. No. 4,857,664 and U.S. Pat. No. 4,935,552 disclose processes for producing ether from starting reactants of a light olefin and water. No external sources of alcohol are used. In contrast, U.S. Pat. No. 4,714,787 discloses producing an ether, methyl isopropyl ether, from methanol and propylene. In U.S. Pat. No. 4,714,787, all the alcohol used in the process is provided through an external source with no alcohol being generated within the process. Finally, U.S. Pat. No. 4,503,263 discloses a process for producing ethers in the presence of acidic superacid catalysts using either (1) an olefin and water, (2) an alcohol, or (3) an olefin and an alcohol as reactants. In the case where an olefin and water are the reactants, the olefin would be hydrated to form an alcohol which would then undergo etherification with the olefin to produce an ether. Where only alcohol is the reactant, bimolecular dehydration of the alcohol would occur to form the ether. Where an olefin and an alcohol are the reactants, the alcohol undergoes etherification with the olefin to form an ether.

The present invention maintains the goal of producing a high octane number product at a low cost by using propylene, a low cost material, and water to form isopropyl alcohol which is then reacted with propylene to form DIPE. At the same time, the invention achieves a goal of incorporating a renewable resource into gasoline by concurrently using ethanol from an independent source as a reactant to form IPEE.

SUMMARY OF THE INVENTION

An object of the invention is to provide a process for concurrently producing diisopropyl ether and isopropyl ethyl ether from water, propylene, and ethanol. The product mixture may be used as a high octane number booster due mainly to the presence of the diisopropyl ether and, to a lesser extent, the isopropyl ethyl ether and, furthermore, the product mixture may be used to incorporate a renewable resource into gasoline since the isopropyl ethyl ether is produced in part from ethanol. Optionally, the product mixture may be passed though an acid removal zone to remove acid, if present. A portion of the product mixture is recycled to the reaction zone to increase the conversion of reactants to products and to maintain a single phase in the reaction zone.

A specific embodiment of the invention is one where propylene and ethylene are separated from the product mixture and recycled to the reaction zone. Another specific embodiment of the invention is one where the propylene to be used in the reactions is contained in a propane and propylene mixture. In this embodiment unreacted propane, propylene, and ethylene are separated from the product mixture and propane is further separated from propylene and ethylene. The propane is collected and the propylene and ethylene are recycled to the reaction zone. Still another specific embodiment of the invention is one where, after the propane, propylene, and ethylene are removed from the product mixture, the mixture is further separated into a water and alcohol-enriched portion which is recycled to the reaction zone and an ether-enriched portion. The ether-enriched portion may be further separated into a diisopropyl ether and isopropyl ethyl ether portion which is collected and a diethyl ether portion which is recycled to the reaction zone to suppress formation of additional diethyl ether.

BRIEF DESCRIPTION OF THE DRAWING

The FIGURE is a schematic representation of the preferred embodiment of the invention of concurrent diisopropyl ether and isopropyl ethyl ether production. The drawing has been simplified by the deletion of a large number of pieces of apparatus customarily employed on a process of this nature which are not specifically required to illustrate the performance of the subject invention.

DETAILED DESCRIPTION OF THE INVENTION

The process of the invention begins with introducing ethanol from an independent source, water, and a hydrocarbon feedstock containing propylene to a reactor containing an acidic catalyst. Introducing ethanol from an independent source, i.e., not from recycle, to the reactor in addition to propylene and water has several benefits. The ethanol, in addition to being a reactant, also functions as a solvent. Propylene has only limited solubility in water, and the presence of ethanol provides for a single phase system. Furthermore, adding ethanol aids in controlling the temperature in the reactor, a task previously accomplished by adding water in great excess. Therefore, the amount of water introduced to the reactor, and consequently the volume of recycle to the reactor, may be reduced.

The relative amounts of water, ethanol, and propylene that are introduced to the reactor are as follows. Suitable water to olefin mole ratios include from about 0.1:1 to about 0.8:1, preferably from about 0.3:1 to about 0.5:1. Suitable ethanol to olefin mole ratios include from about 0.1:1 to about 1:1 with a preferred range of about 0.3:1 to about 0.6:1, depending upon the desired level of IPEE formation. The propylene-containing hydrocarbon feedstock may be a refinery $C_3$ hydrocarbon stream and will most likely be a mixture of propylene and propane. The propylene-containing hydrocarbon feedstock contains at least about 50 mass % propylene, and preferably about 70 mass % propylene. Suitable sources for the propylene-containing hydrocarbon feedstock include, but are not limited to, gas plant off-gas containing propylene, naphtha cracker off-gas containing light olefins, propane dehydrogenation processes, and refinery fluidized catalytic cracked (FCC) propane/propylene streams. The reaction conditions of the reactor include pressures of about 689 to about 10,342 kPa (abs) (about 100 to about 1500 psia), preferably from about 4,826 to about 6,894 kPa (abs) (about 700 to about 1000 psia), and temperatures of about 130° C. to about 180° C., preferably about 135° C. to about 160° C. It is common to slowly increase the operating temperature as the catalyst ages.

The solid acidic catalyst may be any of those commonly used in ether production including activated charcoal, clays, resins, and zeolites. These catalysts are common in the art and do not require discussion here. Examples of acidic ion exchange resin catalysts include sulfonated cation exchange resins such as sulfonated polystyrene resins and sulfonated styrene/divinylbenzene co-polymers. For reference, see U.S. Pat. No. 5,374,301, G.B. 1,176,620, and U.S. Pat. No. 4,182,914. Halogenated strong acid ion exchange resins such as those described in U.S. Pat. No. 4,705,808, U.S. Pat. No. 4,269,943, and U.S. Pat. No. 3,256,250 may also be used. Acidic zeolite catalysts such as those found in U.S. Pat. No. 4,214,107, U.S. Pat. No. 4,499,313, U.S. Pat. No. 5,102,428, and U.S. Pat. No. 5,144,084 may also be used.

As explained below, the following reactions can occur within the reactor:

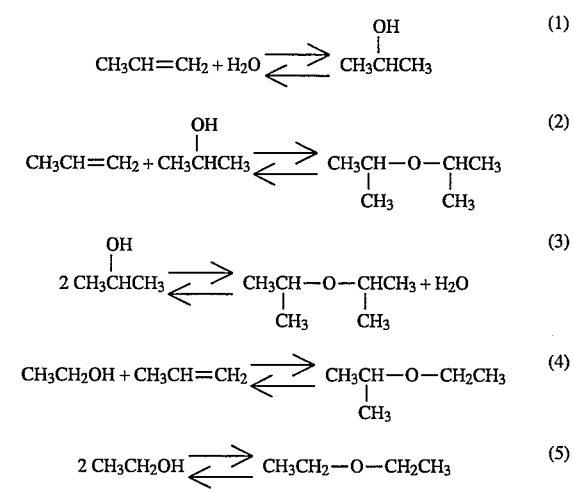

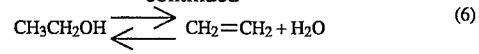

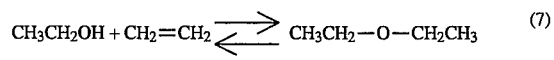

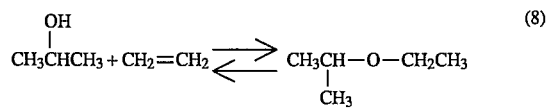

As the propylene and water contact the catalyst, the hydration reaction (1) takes place and isopropyl alcohol (IPA) is formed. As the IPA, ethanol, and propylene contact the catalyst, the etherification reactions (2) and (4) take place and DIPE and IPEE are formed. Reaction (3) can also take place to form DIPE, but it is less preferred due to the increased consumption of IPA as compared to reaction (2). Similarly, ethanol may react with itself to form diethyl ether (DEE) according to equation (5), but this reaction is undesirable since DEE has an extremely low octane number. Ethanol may also dehydrate to form ethylene and water according to equation (6), and the ethylene formed may react with ethanol to form undesired DEE as in equation (7), as well as with IPA to form IPEE as in equation (8). Therefore, the reactor effluent, i.e., product mixture, is a mixture of at least propylene, ethylene, water, IPA, DIPE, IPEE, and DEE. A portion of the reactor effluent is recycled to the reactor to increase the conversion of propylene, water, IPA, and ethanol to DIPE and IPEE.

The remaining reactor effluent may be collected or passed to downstream processing zones to recover product DIPE and IPEE. A preferred downstream processing flowscheme which has the advantage of recycling the DEE and ethylene to suppress additional DEE and ethylene formation is as follows.

A portion of the reactor effluent is passed to a light ends fractionation zone for removal of light compounds such as ethylene, propylene, and propane. The light ends fractionation zone may be operated at temperatures from about 40° C. to about 180° C. and pressures from about 1,379 to about 1,724 kPa (ga) (about 200 to about 250 psig). The light compounds such as ethylene, propylene, and propane are passed to an ethylene-propylene/propane fractionation column where propane is separated from ethylene and propylene. The propane enriched stream is collected, and the ethylene and propylene enriched stream is recycled to the reactor. The ethylene and propylene enriched stream may contain as little as 70 mass % propylene. Since the ethylene and propylene enriched stream may contain as much as about 30 mass % of other components, typically propane, the need for the expensive equipment required to obtain high purity propylene is eliminated. The ethylene is recycled to suppress the formation of additional ethylene. The heavier compounds such as water, IPA, ethanol, IPEE, DEE, and DIPE are passed to an ether/alcohol fractionation zone.

The ether/alcohol fractionation zone is a fractionation column operated at from about 65° C. to about 150° C. and from about 34 to about 345 kPa (ga) (about 5 to about 50 psig) that separates the heavier compounds into an alcohol and water-enriched stream, and an ether-enriched stream. The alcohol and water-enriched stream contains the IPA, ethanol, and water, and the ether-enriched stream contains the DIPE, IPEE, and DEE. The alcohol and water stream is recycled to the reactor to increase the conversion of IPA and ethanol to DIPE and IPEE and to help maintain a single phase in the reactor.

The ether-enriched stream is passed to an ether fractionation zone which is a fractionation column operated at temperatures from about 40° C. to about 100° C. and pressures of about 138 to about 345 kPa (ga) (about 20 to about 50 psig). In the ether fractionation zone, a DIPE and IPEE-enriched stream is separated from a DEE-enriched stream. The DIPE and IPEE-enriched stream is collected as product and may be blended with gasoline. The DEE-enriched stream is recycled to the reactor to suppress the formation of additional DEE.

An optional variation of the above flowscheme is one where the reactor effluent is passed to an acid removal zone prior to recycling or downstream processing. This variation applies when a strongly acidic ion exchange resin is used as the catalyst. Strongly acidic ion exchange resin catalysts may undergo hydrolysis of the acid groups causing the transfer of acid into the reactor effluent: If the acid is not removed, the catalyst and downstream process units may be adversely affected.

The acid removal zone may contain any solid particles capable of removing the acid from the reactor effluent. For example, the solid particles may be alkaline metal oxides, base ion exchange resins, basic organically-bridged polysilsesquioxanes particles, activated carbon, or any other strongly basic inorganic compounds with reasonable thermal stability considering the reactor effluent will be at temperatures from about 130° C. to about 180° C. Examples of suitable base ion exchange resins include strong-base quaternary ammonium anion exchangers, amine-type weak base anion exchangers, or pyridine-type anion exchangers. Specific suitable commercial base ion exchange resins include Amberlite® IRA-67, Amberlite® IRA-68, Amberlite® IRA-93, Amberlite® CG-420, Amberlite® IRA-410, Amberlite® IRA-900, Amberlite® IRA-904, Duolite A-7, Duolite A-368, Amberlyst A-21, Amberlyst A-26, Amberlyst A-27, Dowex® 1X2-100, Dowex® 1X2-200, Dowex® 1X2-400, Dowex® 1X8-50, Dowex® 1X8-100, Dowex® 1X8-200, and Dowex® 1X8-400 which are sold by Rohm and Haas, Diamond Shamrock, or Dow. The more preferred resins are those that are stable at higher temperatures such as Amberlite® IRA-67 and Amberlite® IRA-68. These types of base ion exchange resins are readily commercially available and are very well known in the art and do not require discussion here. See generally, *Ullmann's Encyclopedia of Industrial Chemistry*, 5th ed.; Elvers, B., Hawkins, S., Ravenscroft, M., Schulz, G., Eds.; Wienham: Cambridge, New York, Vol. A14, pp. 397–398. Examples of acid removal zones may be found in U.S. Pat. No. 4,182,914, and U.S. Pat. No. 5,371,301.

As the reactor effluent is introduced to the acid removal zone, the acid carried in the reactor effluent contacts solid particles and is removed from the stream. The acid-depleted stream may then be recycled and/or passed to downstream processing units without adverse effects.

Without intending any limitation of the scope, of the present invention and as merely illustrative, the invention is explained below in specific terms as applied to a specific embodiment of the invention which is based on a design for a commercial scale unit. Referring to the FIGURE, a feed 2 of 45 mass % propylene, 20 mass % propane, 24 mass % ethanol, and 11 mass % water, stream 22 which is enriched in DEE, stream 30 which is enriched in propylene and ethylene, stream 32 which contains water, propane, propylene, ethylene, ethanol, IPA, DIPE, IPEE, and DEE, and stream 34 which is enriched in water, IPA, and ethanol, are combined and introduced to hydration and etherification reactor 4 which contains sulfonated styrene/divinylbenzene co-polymer ion exchange resin catalyst. Reactor 4 is operated at about 150° C. and about 6,895 kPa (ga) (about 1000 psig). In reactor 4 the hydrolysis of propylene is catalyzed and IPA is formed, and IPA and ethanol are catalytically reacted with propylene to form DIPE and IPEE. Some ethanol may react to form the undesired DEE or ethylene. Therefore, the reactor effluent 6 contains water, propane, propylene, ethylene, ethanol, IPA, DIPE, IPEE, and DEE. Reactor effluent 6 is divided into two streams, one portion, stream 32, is recycled to the reactor, and one portion, stream 8, is passed to a light ends fractionation column 10. Fractionation in the light ends fractionation column 10 at 40°–180° C. and 1,379–1,724 kPa (ga) (200–250 psig) results in an ethylene, propylene, and propane enriched stream 12 which is passed to an ethylene-propylene/propane fractionation column 26, and a water, IPA, ethanol, DIPE, IPEE, and DEE enriched stream 14 which is passed to a water-alcohol/ether fractionation column 16. In ethylene-propylene/propane fraction column 26, the ethylene, propylene, and propane enriched stream 12 is separated by fractionation at 40°–60° C. and 1,724–2,413 kPa (ga) (250–350 psig) into a propane enriched stream 28 which is collected and a propylene and ethylene-enriched stream 30 which contains about 80 mass % propylene and is recycled to reactor 4. In water-alcohol/ether fractionation column 16, water, IPA, ethanol, DIPE, IPEE, and DEE enriched stream 14 is separated by fractionation at 40°–100° C. and 34–172 kPa (ga) (5–25 psig) into IPA, ethanol, and water-enriched stream 34 which is recycled to reactor 4, and a DIPE, IPEE, and DEE-enriched stream 18 which is passed to an ether fractionation column 20. In ether fractionation column 20, DIPE, IPEE, and DEE enriched stream 18 is separated by fractionation at 40°–100° C. and 34–345 kPa (ga) (5–50 psig) into a DIPE and IPEE-enriched product stream 24 which is collected, and a DEE enriched stream 22 which is recycled to reactor 4.

It must be emphasized that the above description is merely illustrative of a preferred embodiment and is not intended as an undue limitation on the generally broad scope of the invention. Moreover, while the description is narrow in scope, one skilled in the art will understand how to extrapolate to the broader scope of the invention. For example, the process flowscheme where the reactor effluent is passed through an acid removal zone to remove acid before recycling or downstream processing or where the propylene feedstock contains ethane which may be vented from the process can be readily extrapolated from the foregoing description.

EXAMPLE

Two autoclave liners were each packed with 100 cc of sulfonated styrene/divinylbenzene resin catalyst. A charge of 120 g ethanol was added to each liner and each liner was placed in a stirred autoclave. Each autoclave was charged further with 180 g of propylene and pressurized to about 1,379 kPa (ga) (200 psig) and heated to about 140° C. These conditions were maintained for 8 hours and the resulting normally liquid products contained the compounds as listed in the table as determined by gas chromatography.

TABLE

| COMPOUND | RUN 1 | RUN 2 |
|---|---|---|
| Propylene | 2.35 wt % | 3.47 wt % |
| Ethanol | 0.73 wt % | 0.49 wt % |
| Acetone | 0.32 wt % | 0.39 wt % |
| Isopropyl Alcohol | 3.91 wt % | 2.42 wt % |
| Diethyl Ether | 23.86 wt % | 27.48 wt % |
| Isopropyl Ethyl Ether | 39.58 wt % | 35.72 wt % |
| Hexane | 4.84 wt % | 4.06 wt % |
| Diisopropyl Ether | 20.17 wt % | 19.85 wt % |
| n-Propyl Isopropyl Ether | 0.58 wt % | 1.52 wt % |
| $C_9+$ | 3.56 wt % | 4.47 wt % |

What is claimed is:

1. A process of concurrently producing diisopropyl ether and isopropyl ethyl ether comprising:
   a. reacting, in a reaction zone at reaction conditions ranging from about 100 to about 1500 psia and from about 130° C. to about 180° C., water, ethanol from an independent source, and propylene of a feedstock containing at least 50 mass % propylene in the presence of an acidic catalyst selected from the group consisting of activated charcoal, clays, resins, and zeolites, to afford a product mixture comprising water, isopropyl alcohol, ethanol, diisopropyl ether, isopropyl ethyl ether, diethyl ether, ethylene, and propylene;
   b. passing the product mixture to an acid removal zone to remove acid; and
   c. recycling a first portion of the product mixture to the reaction zone and collecting a second portion of the product mixture.

2. The process of claim 1 further comprising:
   a. passing the second portion to a first separation zone to afford a propylene and ethylene-enriched stream and an isopropyl alcohol, ethanol, diisopropyl ether, isopropyl ethyl ether and water-enriched stream; and
   b. recycling the propylene and ethylene-enriched stream to the reaction zone and collecting the isopropyl alcohol, ethanol, diisopropyl ether, isopropyl ethyl ether and water-enriched stream.

3. The process of claim 1 where the feedstock is a mixture of propane and propylene.

4. The process of claim 1 where the feedstock is a mixture of propane and propylene, the process further comprising:
   a. passing the second portion to a first separation zone to afford a propane, propylene and ethylene-enriched stream, and an isopropyl alcohol, ethanol, diisopropyl ether, isopropyl ethyl ether and water-enriched stream which is collected; and
   b. passing the propane, propylene and ethylene-enriched stream to a second separation zone to afford a propylene and ethylene-enriched stream which is recycled to the reaction zone, and a propane enriched stream which is collected.

5. The process of claim 4 further comprising:
   a. passing the isopropyl alcohol, ethanol, diisopropyl ether, isopropyl ethyl ether and water-enriched stream to a third separation zone to afford an isopropyl alcohol, ethanol and water-enriched stream which is recycled to the reaction zone and a diisopropyl ether, isopropyl ethyl ether and diethyl ether-enriched stream; and
   b. passing the diisopropyl ether, isopropyl ethyl ether, and diethyl ether-enriched stream to a fourth separation zone to afford a diethyl ether-enriched stream which is recycled to the reaction zone, and a diisopropyl ether and isopropyl ethyl ether-enriched stream which is collected.

6. The process of claim 1 where the ethanol and the propylene are present in a ratio of 0.1:1 to about 1:1.

7. The process of claim 1 where the ethanol and the propylene are present in a ratio of 0.3:1 to about 0.6:1.

8. The process of claim 1 where the water and the propylene are present in a ratio of about 0.1:1 to about 0.8:1.

9. The process of claim 1 where the water and the propylene are present in a ratio of about 0.3:1 to about 0.5:1.

10. A process of concurrently producing diisopropyl ether and isopropyl ethyl ether comprising:
    a. reacting, in a reaction zone at reaction conditions ranging from about 100 to about 1500 psia and from about 130° C. to about 180° C., water, ethanol from an independent source, and propylene of a feedstock containing at least 50 mass % propylene in the presence of an acidic catalyst selected from the group consisting of activated charcoal, clays, resins, and zeolites, to afford a product mixture comprising water, isopropyl alcohol, ethanol, diisopropyl ether, isopropyl ethyl ether, diethyl ether, ethylene, and propylene; and
    b. recycling a first portion of the product mixture to the reaction zone and collecting a second portion of the product mixture.

11. The process of claim 10 further comprising:
    a. passing the second portion to a first separation zone to afford a propylene and ethylene-enriched stream and an isopropyl alcohol, ethanol, diisopropyl ether, isopropyl ethyl ether and water-enriched stream; and
    b. recycling the propylene and ethylene-enriched stream to the reaction zone and collecting the isopropyl alcohol, ethanol, diisopropyl ether, isopropyl ethyl ether and water-enriched stream.

12. The process of claim 10 where the feedstock is a mixture of propane and propylene.

13. The process of claim 10 where the feedstock is a mixture of propane and propylene, the process further comprising:
    a. passing the second portion to a first separation zone to afford a propane, propylene and ethylene-enriched stream, and an isopropyl alcohol, ethanol, diisopropyl ether, isopropyl ethyl ether and water-enriched stream which is collected; and
    b. passing the propane, propylene and ethylene-enriched stream to a second separation zone to afford a propylene and ethylene-enriched stream which is recycled to the reaction zone, and a propane-enriched stream which is collected.

14. The process of claim 13 further comprising:
    a. passing the isopropyl alcohol, ethanol, diisopropyl ether, isopropyl ethyl ether and water-enriched stream to a third separation zone to afford an isopropyl alcohol, ethanol and water-enriched stream which is recycled to the reaction zone and a diisopropyl ether, isopropyl ethyl ether and diethyl ether-enriched stream; and
    b. passing the diisopropyl ether, isopropyl ethyl ether, and diethyl ether-enriched stream to a fourth separation zone to afford a diethyl ether-enriched stream which is recycled to the reaction zone, and a diisopropyl ether and isopropyl ethyl ether-enriched stream which is collected.

15. The process of claim 10 where the ethanol and the propylene are present in a ratio of about 0.1:1 to about 1:1.

16. The process of claim 10 where the ethanol and the propylene are present in a ratio of about 0.3:1 to about 0.6:1.

17. The process of claim 10 where the water and the propylene are present in a ratio of about 0.1:1 to about 0.8:1.

18. The process of claim 10 where the water and the propylene are present in a ratio of about 0.3:1 to about 0.5:1.

* * * * *